United States Patent
Reaux

(10) Patent No.: US 8,282,662 B2
(45) Date of Patent: Oct. 9, 2012

(54) MEDICAL SHEATH FOR SCALPEL HANDLE WITH RETRACTABLE BLADE GUARD

(75) Inventor: Brian K. Reaux, Red Oak, TX (US)

(73) Assignee: Ansell Sandell Medical Solutions LLC, Chatsworth, CA (US)

( * ) Notice: Subject to any disclaimer, the term of this patent is extended or adjusted under 35 U.S.C. 154(b) by 455 days.

(21) Appl. No.: 11/346,501

(22) Filed: Feb. 2, 2006

(65) Prior Publication Data

US 2010/0063522 A1 Mar. 11, 2010

Related U.S. Application Data

(60) Provisional application No. 60/649,430, filed on Feb. 2, 2005.

(51) Int. Cl.
*A61B 17/32* (2006.01)

(52) U.S. Cl. .......................... 606/167; 30/272.1; 30/327

(58) Field of Classification Search .................. 606/167, 606/170, 172; 30/272.1, 273, 285, 286, 266, 30/327

See application file for complete search history.

(56) References Cited

U.S. PATENT DOCUMENTS

| | | |
|---|---|---|
| 3,943,627 A | 3/1976 | Stanley, Jr. |
| 4,523,379 A | 6/1985 | Osterhout et al. |
| 4,757,612 A | 7/1988 | Peyrot |
| 5,071,426 A | 12/1991 | Dolgin et al. |
| 5,139,507 A | 8/1992 | Dolgin et al. |
| 5,312,429 A | 5/1994 | Noack |
| 5,330,492 A | 7/1994 | Haugen |
| 5,496,340 A | 3/1996 | Abidin et al. |
| 5,527,329 A | 6/1996 | Gharibian |
| 5,620,454 A | 4/1997 | Pierce et al. |
| 5,662,669 A | 9/1997 | Abidin et al. |
| 5,683,407 A * | 11/1997 | Jolly et al. ..................... 606/181 |
| 5,752,968 A * | 5/1998 | Jolly et al. ..................... 606/167 |
| 5,792,162 A | 8/1998 | Jolly et al. |
| 5,827,309 A | 10/1998 | Jolly et al. |
| 5,868,771 A * | 2/1999 | Herbert et al. ................ 606/167 |
| 5,878,501 A | 3/1999 | Owens et al. |
| 5,919,201 A | 7/1999 | Carter et al. |
| 5,938,675 A | 8/1999 | Gharibian |
| 5,938,676 A | 8/1999 | Cohn et al. |
| 5,941,892 A | 8/1999 | Cohn et al. |
| 6,015,419 A | 1/2000 | Strome et al. |
| 6,053,929 A | 4/2000 | Cohn et al. |
| 6,884,240 B1 * | 4/2005 | Dykes ............................... 606/1 |
| 7,022,128 B2 * | 4/2006 | Morawski et al. ............ 606/167 |

(Continued)

FOREIGN PATENT DOCUMENTS

WO 2004084706 10/2004

OTHER PUBLICATIONS

Dictionary.com, dictionary results for "section", retrieved Nov. 2, 2010 from http://dictionary.reference.com/browse/section.*

(Continued)

*Primary Examiner* — Victor Nguyen
(74) *Attorney, Agent, or Firm* — Moser Taboada

(57) ABSTRACT

A scalpel device has a metal shank having a blade carrier configured holding a scalpel blade. A sheath is configured for receiving the scalpel shank. The shank is rigidly coupled to the sheath. A retractable blade guard is movably coupled to the sheath. The blade guard is movable between retracted and extended positions wherein the scalpel blade is selectively covered or exposed.

6 Claims, 4 Drawing Sheets

U.S. PATENT DOCUMENTS

| | | | |
|---|---|---|---|
| 7,153,317 B2 * | 12/2006 | Kanodia et al. | 606/167 |
| 7,156,231 B1 | 1/2007 | Austria | |
| 7,159,713 B1 | 1/2007 | Austria | |
| D568,475 S | 5/2008 | Sandel et al. | |
| 2004/0186496 A1 | 9/2004 | Sandel et al. | |

OTHER PUBLICATIONS

Dictionary.com, definition of affixed, http://dictionary.reference.com/browse/affixed.*

E-mail dated Nov. 18, 2009 from Brian Reaux referencing U.S. Appl. No. 11/346,501 and U.S. Appl. No. 11/961,004.

Publication: Surgical Products, Jan. 2006, back cover showing "Disposable Safety Scalpel."

Fax letter from Brian Reaux asserting derivation/inventorship, Apr. 11, 2008.

* cited by examiner

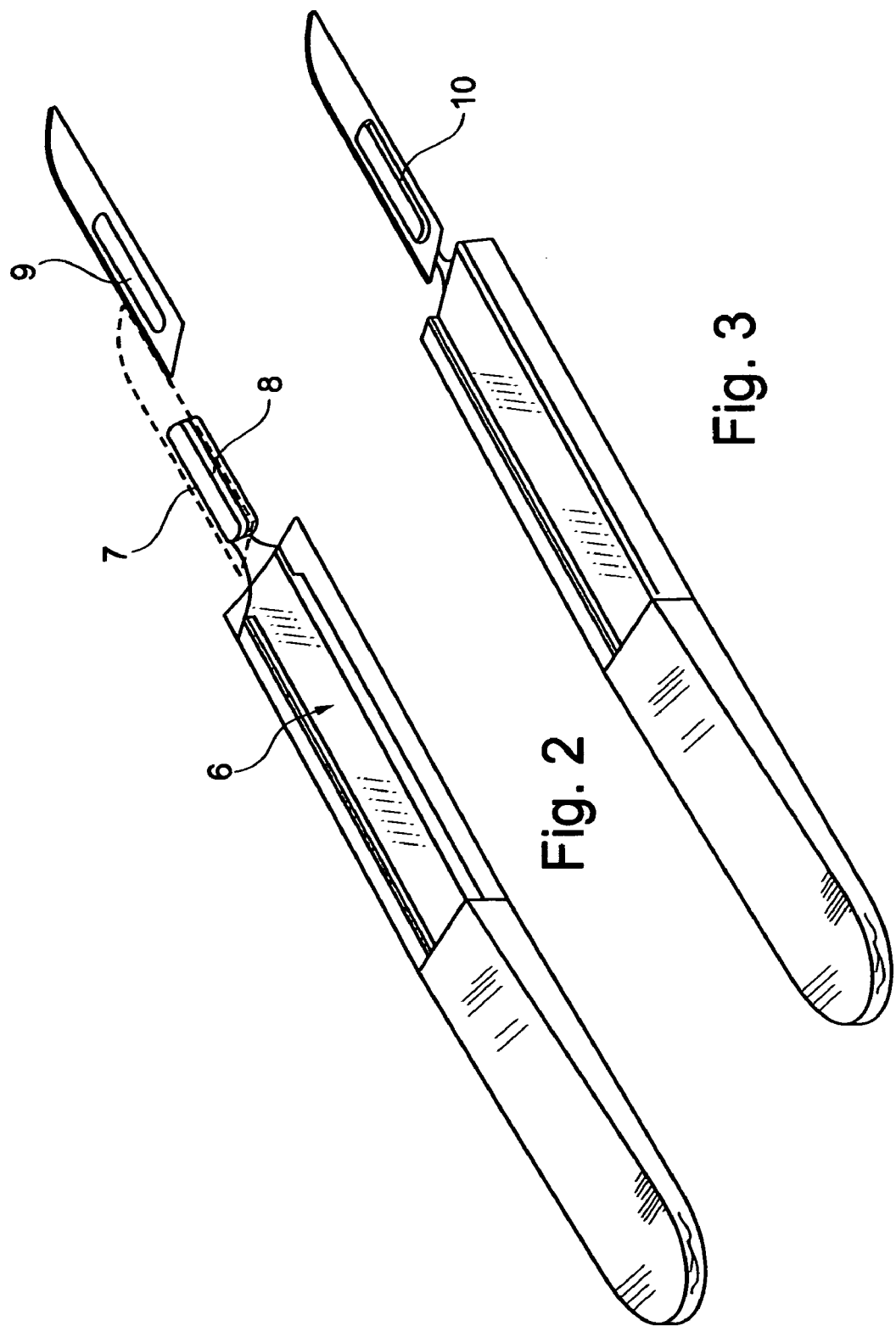

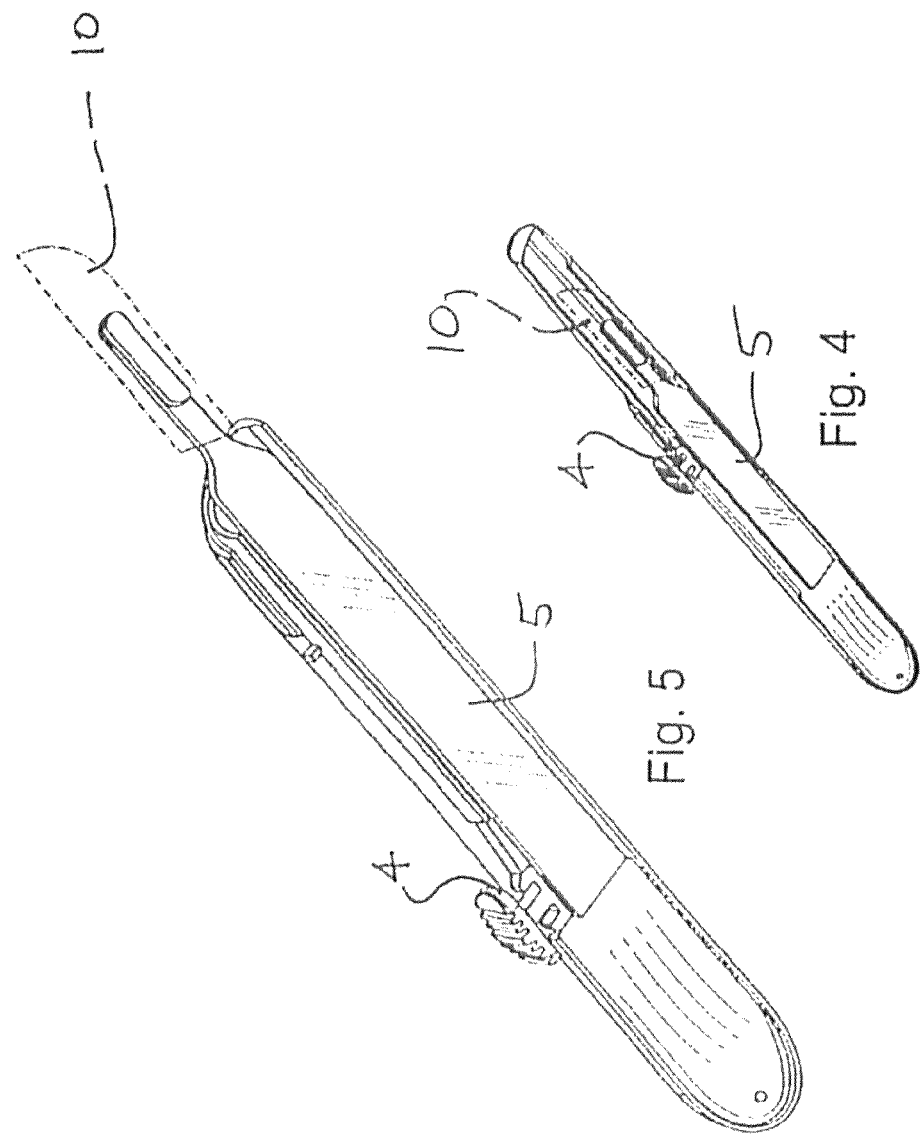

MEDICAL SHEATH FOR SCALPEL HANDLE WITH RETRACTABLE BLADE GUARD

This application claims the benefit of U.S. Provisional Application No. 60/649,430, filed Feb. 2, 2005, which is hereby incorporated by reference in its entirety.

BACKGROUND

Disposable scalpels are typically provided with a plastic handle to which a scalpel blade is coupled to the plastic components of the handle. These scalpels are very light compared to conventional non-disposable or reusable full metal scalpels. Those used to the heavier reusable scalpels may find this undesirable. Furthermore, in use, the plastic materials may be prone to breakage, which is undesirable. In practice, several disposable scalpels may have to be used because of this tendency toward breakage.

BRIEF DESCRIPTION OF THE DRAWINGS

For a more complete understanding of the present invention, reference is now made to the following descriptions taken in conjunction with the accompanying figures, in which:

FIG. 2 is a perspective view of the scalpel device of FIG. 1, shown with the handle sheath partially section and a blade of the device disengaged and exploded from the device;

FIG. 3 is a perspective view of the scalpel device of FIG. 2, shown with the blade engaged with a blade post of the scalpel device;

FIG. 4 is a longitudinal cross-sectional perspective view of the scalpel device of FIG. 1, shown with the blade guard in the extended position;

FIG. 5 is a longitudinal cross-sectional perspective view of the scalpel device of FIG. 4, shown with the blade guard in a retracted position.

DETAILED DESCRIPTION

Figure 1:
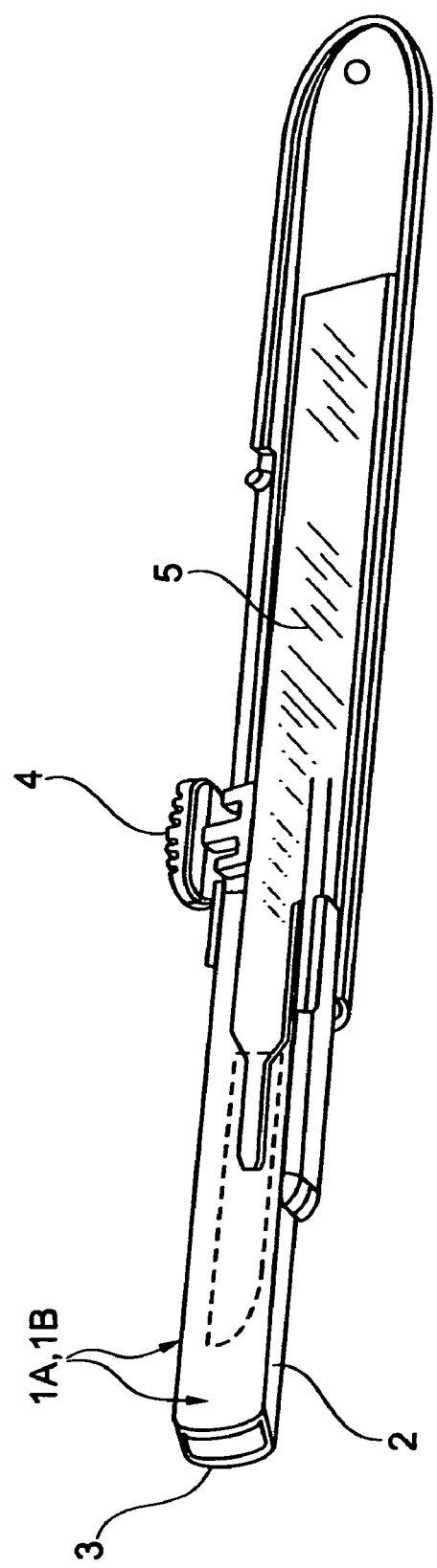
FIG. 1 is a perspective view of a scalpel device having a retractable blade guard assembly, shown with handle sheath partially sectioned and the blade guard in an extended position.

Referring to FIG. 1, a blade guard assembly of a scalpel device may formed from clear plastic blade guard wall sections 1A, 1B that are joined along the edge or wall 2. The sections 1A, 1A are spaced apart to define a longitudinal slot that receives a blade of the scalpel device and terminates in an opening 3 at the end of the blade guard to allow passage of a scalpel blade therethrough. The sections 1A, 1B may be clear plastic material to allow visual perception therethrough.

The blade guard assembly is provided with a thumb member or projection 4 that is coupled to the blade guard and may be manually manipulated to move the blade guard between retracted and extended positions. The blade guard assembly is movably coupled to a scalpel 5 so that the blade guard can be moved forward over the scalpel blade 10 when in an extended position to prevent inadvertent contact with the blade 10 and moved rearward away from the blade 10 so that it is exposed.

The scalpel 5 includes a handle shank 6 (FIGS. 2 and 3) having a blade post 7. The shank and post may be formed from steel or other suitable metal to provide strength and add weight to the scalpel and may be formed as an integral unit. Alternatively, the shank and post may be a plastic, polymeric or other non-metal material with the shank and post being integrally formed together. The shank may be the same or similar to the weight of a conventional reusable metal scalpel handle. In fact, a traditional metal scalpel could be used and incorporated into the sheath, as it is described below. The shank 6, however, may be smaller and weigh less than traditional metal scalpel handles to reduce material usage, eight and cost of the construction of the scalpel, thus facilitating its disposability. The blade post 7 may be of conventional design to facilitate releasable mounting and removal of conventional scalpel blades of the type having an opening or aperture 9 for engagement with locking members 8 of the blade post 7. Alternatively, the blade 10 may be permanently mounted to the post 7 for single use.

Figure 6:
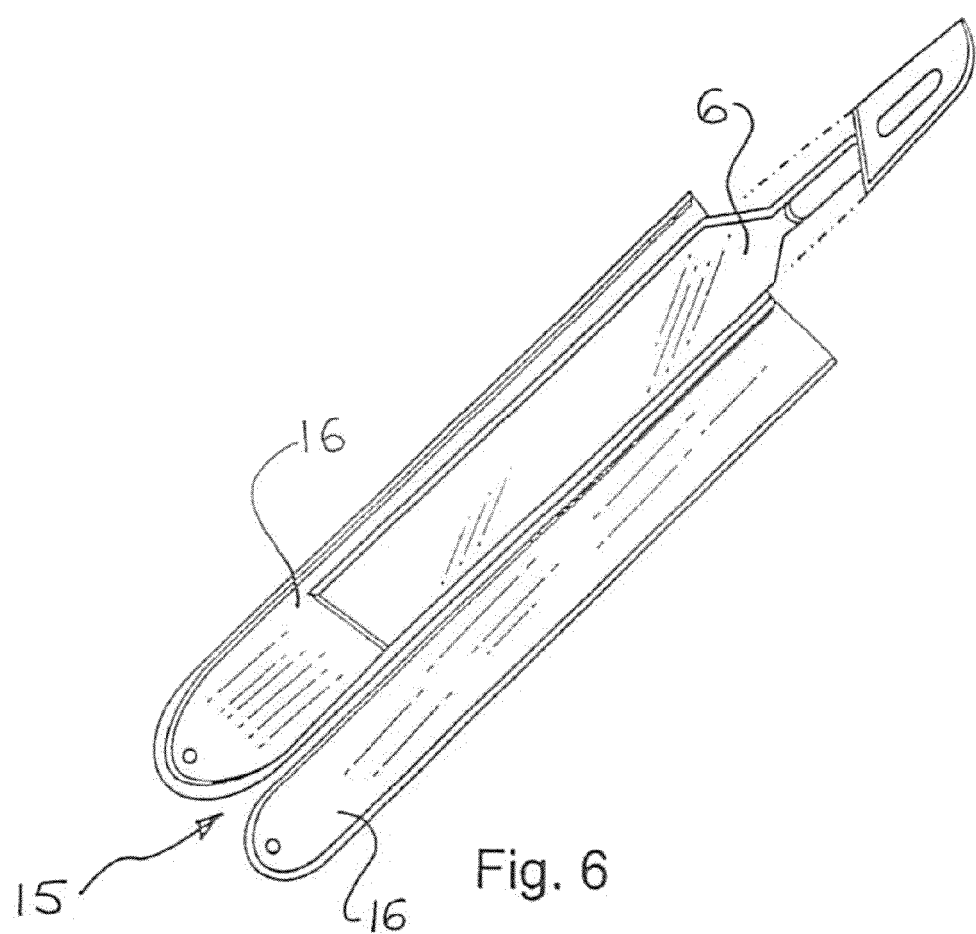
FIG. 6 is a perspective view of the scalpel device of FIG. 1 without the blade guard assembly and showing the longitudinal sections of the handle sheath.

The shank 6 is housed within a plastic or polymeric handle sheath 15 (FIG. 6) that surrounds the shank 6. At least a portion of the shank 6 longitudinally coextends with the sheath 15. The sheath may be formed into two halves or longitudinal sections 16. The shank is rigidly attached to the sheath. All or a portion of the shank 6 may be securely sandwiched or be embedded within the plastic material of the sheath to provide rigidity and strength. The blade post 7 projects from the sheath 15. The exterior of the sheath 15 may be configured or shaped as a conventional scalpel blade handle to facilitate handling and use. The shank 6 may thus be formed from less material than a conventional non-disposable scalpel that has a full metal or steel handle. This allows that scalpel to be manufactured at lower cost and allows that scalpel device to be disposable. The shank 6 may be press molded or stamped out for lower manufacturing costs. The shank, however, which extends and is securely fastened to the sheath 15, provides additional strength that is not found in full plastic handle scalpels.

The blade guard assembly is movably coupled to the plastic sheath 15. Slots and grooves formed in the plastic material of the sheath allow engagement of the guard assembly with the handle sheath and may limit forward and rearward movement of the blade guard assembly.

As shown in FIGS. 4 and 5, the sheath 15 may have a forward opening or chamber for receiving the blade guard of the blade guard assembly when the guard is in the retracted position. As shown in FIG. 5, the blade guard is shown in the fully retracted position. When in this position, the thumb member 4 or portions thereof may abut against a rearward end of a longitudinal slot formed in an upper wall the sheath 15. When the thumb member 4 is moved forward along the slot, the blade guard is forced out of the forward chamber of the sheath 15 so that the blade guard covers the blade 10, as shown in FIG. 4. The thumb member 4 or portions thereof may abut or engage a forward end of the longitudinal slot formed in the upper wall of the sheath 15 or other limit or stop device to prevent further forward movement of the guard assembly. Releasable detents or locking members may engage the blade assembly when in the fully extended or retracted positions. The blade guard may extend from 1 mm to 10 mm or more beyond the scalpel blade 10 to prevent inadvertent contact with the blade tip. The wall 2 also prevents contact with the cutting edge of the blade 10.

In an alternate embodiment, the blade post 7 may be incorporated or integrated with the sheath and the shank 6 eliminated. Additional weights may be used to provide weight to the shank 6.

While the embodiment shown shows the blade guard being received within the handle sheath, it could also be incorporated so that the guard assembly is exterior to the sheath 15. In such a configuration, the guard assembly would be retracted or extended over the forward end of the sheath.

The blade guard is sized, shaped or otherwise configured to fully cover the scalpel blade when it is secured to the handle.

Because the scalpel device is constructed primarily from plastic material it may be disposable and may be disposed of as a unit. The scalpel device may also be reusable or have limited reusability (i.e two or more uses before disposal). The device may be sterilized and provided in sterilized packaging. If desired, the construction of the scalpel device with a conventional blade post, allows the blade to be changed. This differs from other disposable scalpels do not allow the scalpel blade to be replaced. This also allows different style blades to be used or allows replacement of blades that have been dulled or damaged. Additionally, the plastic materials of the prior art disposable scalpels make them prone to breakage. The metal handle or shank portion that extends into the handle sheath provides strength that is not found in the plastic handles of prior art disposable scalpels. The metal handle or shank portion also adds weight and provide a better feel, which is more like that of reusable full metal handle scalpels, without requiring the use of separate weighting members. The blade guard may be readily moved between retracted and extended positions with one hand.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

I claim:

1. A scalpel handle, comprising:
a shank having an integral blade carrier post configured for holding a scalpel blade;
a handle sheath having two longitudinal sections formed of a given material, with the shank securely fastened to the sheath by being sandwiched between the two longitudinal sections of the sheath so that the shank is surrounded by and securely embedded within the material of the two longitudinal sections of the handle sheath, the shank coextending substantially the length of the handle sheath; and
a retractable blade guard movably coupled to the handle sheath, the blade guard movable between retracted and extended positions, wherein the blade carrier post can be selectively covered or exposed; wherein the retractable blade guard has a transparent section; further the retractable blade guard slidable in a longitudinal slot in the handle sheath, and with a back end of the shank generally aligned under a back end of the slot.

2. A scalpel handle, comprising:
a shank;
a scalpel blade carrier post at a front end of the shank;
a handle sheath formed of a given material, with a back end of the shank contained within the handle sheath, and with the front end of the shank extending out of the handle sheath, the shank securely fastened to the sheath by being sandwiched between two longitudinal sections of the sheath so that the shank is surrounded by and securely embedded within the material of the sheath; and
a retractable blade guard slidably attached to the sheath, the blade guard slidable between a retracted position wherein the blade post is exposed, and an extended position wherein the blade carrier post is shielded; wherein the retractable blade guard has a transparent section, further the retractable blade guard includes generally parallel wall sections that defined a slot and with the wall sections being joined together along the edge.

3. The scalpel handle of claim 2 with a metal shank having a length more than half of the length of the handle sheath.

4. The scalpel handle of claim 2 with the blade guard adjacent to the back end of the shank when the blade guard is in the retracted position.

5. The scalpel handle of claim 2 with the handle sheath comprising two longitudinal sections and with the shank enclosed within the longitudinal sections.

6. A scalpel handle, comprising:
a shank having a front section and a back section, with the front section including a scalpel blade carrier post;
a handle sheath formed of a given material with the back section of the shank contained within and securely fastened to the sheath by being sandwiched between two longitudinal sections of the sheath so that the shank is surrounded by and securely embedded within the material of the two longitudinal sections of the handle sheath; and
a retractable blade guard slidably attached to a front end of the sheath; wherein the retractable blade guard has a transparent section, further the retractable blade guard includes generally parallel wall sections that define a slot and with the wall sections being joined together along one edge.

* * * * *